United States Patent [19]

Pei et al.

[11] Patent Number: 5,783,189
[45] Date of Patent: Jul. 21, 1998

[54] METHOD FOR TREATING ALCOHOL DEPENDENCE

[75] Inventors: Yue-Hu Pei, Durham; David Overstreet, Chapel Hill; Amir Hosein Rezvani, Chapel Hill; David Yue-Wei Lee, Chapel Hill, all of N.C.

[73] Assignee: Natural Pharmacia International, Inc., Research Triangle Park, N.C.

[21] Appl. No.: 636,347

[22] Filed: Apr. 23, 1996

[51] Int. Cl.⁶ .......................... A61K 35/78; A61K 39/385
[52] U.S. Cl. .......................... 424/195.1; 514/811
[58] Field of Search .......................... 424/195.1; 514/811

[56] References Cited

U.S. PATENT DOCUMENTS

| | | | |
|---|---|---|---|
| 5,204,369 | 4/1993 | Vallee et al. | 514/456 |
| 5,324,516 | 6/1994 | Pek et al. | 424/195.1 |
| 5,482,712 | 1/1996 | Kim et al. | 424/195.1 |
| 5,547,671 | 8/1996 | Duthinh | 424/195.1 |

OTHER PUBLICATIONS

Overstreet et al., "Suppression of Alcohol Intake after . . . ", *Alcohol. Clin. Exp. Res.*, 20(2):221–227, 1996.
Lin et al., "Isoflavonoid Compounds Extracted from *Pueraria lobata* . . . ", *Alcohol. Clin. Exp. Res.*, 20(4):659–663, (19960.
Keung et al., "Daidzin Suppresses ethanol consumption by Syrian . . . ", *Proc. Natl. Acad. Sci. USA*, vol. 92:8990–8993, Sep. 1995.
Kinjo et al., "Studies on the Constituents of *Pueraria lobata*. III . . . ", *Chem. Pharm. Bull.*, 35(12):4846–4850, 1987.

*Primary Examiner*—Marianne M. Cintins
*Assistant Examiner*—M. Moezie
*Attorney, Agent, or Firm*—Millen, White, Zelano & Branigan, P.C.

[57] ABSTRACT

Isoflavonoids containing a carbon-carbon linked β-D-glucose moiety at the C-8 position and isolated from the Chinese herbal plant *Pueraria lobata* are useful for treating alcohol dependence.

11 Claims, 4 Drawing Sheets

5,783,189

METHOD FOR TREATING ALCOHOL DEPENDENCE

BACKGROUND OF THE INVENTION

1. Field of the Invention

The present invention relates to methods of treating and preventing alcohol dependence with a class of isoflavonoids containing a carbon-carbon linked β-D-glucose moiety at the C-8 position.

2. Discussion of the Background

Alcoholism and alcohol related diseases are threatening human health at an alarming rate and are posing major medical, social, and economic problems. In the United States alone, 10% of the population is affected by alcoholism and an even higher percentage consume excessive amounts of alcohol. Recently, adolescent drinking has become a serious threat to the health of our next generation. Thus, there is an urgent need for the development of effective therapeutic agents for treating alcohol abuse and alcoholism.

Despite greater effort devoted to treatment research in recent years, definitive, effective remediation of alcoholism remains a challenging goal. Much current research in the treatment of alcoholism has been centered around the clinical use of drugs in the management of alcohol withdrawal. The benzodiaze-pines are most frequently used and newer medications are being investigated (Litten and Allen, 1991; O'Malley et al., 1992a; Soyka, 1995a,b). The antidipsotropic agent disulfiram was the first and until recently the only drug approved for the treatment of alcohol dependence in the United States.

Recent pharmacological studies on the effect of alcohol on various neurotransmitter systems in the brain have led to the development of new pharmacotherapy for alcoholism (Soyka, 1995). Dopamine agonists and antagonists, serotonergic agents, glutamate antagonists, opiate antagonists, ALDH inhibitors, and calcium blockers have been reported to suppress alcohol drinking in alcoholic humans and alcohol-preferring rats (Banys, 1988; Lawrin et al., 1986; McBride et al., 1989; Naranjo et al., 1990; Rezvani et al., 1990, 1991; Sellers et al., 1992). For instance, naltrexone, an opioid receptor antagonist, was recently approved in the United States for the treatment of alcohol-dependent patients. Naltrexone in combination with psychotherapy showed encouraging results in several clinical trials (Berg et al., 1990; O'Malley et al., 1992a;b; Volpicelli et al., 1990, 1992).

The Chinese herbal medicine XJL ("NPI-028") has long been used to reduce the intoxication that results from ingestion of an excessive amount of alcohol. However, the ability of XJL to reduce alcohol consumption was neither reported nor studied previously and the active ingredients therein have not heretofore been isolated or identified. NPI-028 contains several isoflavonoids, including some of the compounds of this invention, and is produced from several Chinese herbal plants, including *Pueraria lobata* and *Citrus reticulata*, as recorded in an ancient Chinese materia medica entitled Ben Cho Gang Mu (Li, 1590-1596 A.D.).

OBJECTS OF THE INVENTION

It is an object of this invention to provide a method of treating and preventing alcohol dependence with an isoflavonoid-C-glycoside or mixture of same.

Another object is to provide a pharmaceutical composition comprising one or more isoflavonoids, in isolated form substantially free from other isoflavonoids, and pharmaceutical compositions comprising them which are useful for the treatment of alcohol dependence.

Upon further study of the specification and appended claims, further objects and advantages of this invention will become apparent to those skilled in the art.

SUMMARY OF THE INVENTION

In a method of use aspect, this invention relates to a method of ameliorating or preventing alcohol dependence which comprises administering in successive spaced doses to an individual desiring to reduce alcohol dependence, a pharmaceutical composition comprising, in admixture with a pharmaceutically acceptable carrier, an amount effective to reduce the alcohol consumed by the individual of at least one isoflavonoid-C-glycoside of formula (I):

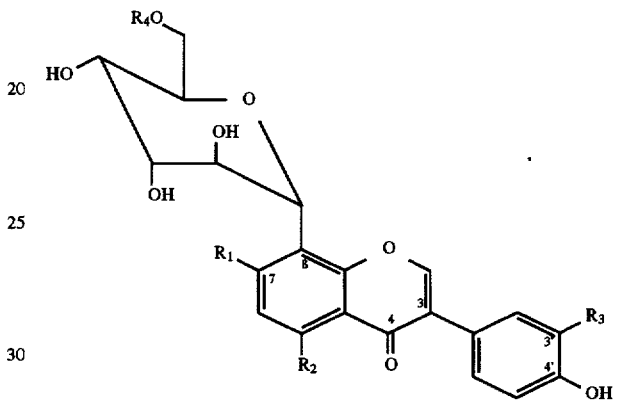

$R_1$ = H, OH
$R_2$ = H, OH
$R_3$ = H, OH, OR'(R' = $CH_3$, $C_2H_5$)
$R_4$ = H, or glucose or 1-6-apiosyl wherein $R_1$=H or OH; $R_2$=H or OH; $R_3$=H, OH or OR' wherein R' is lower alkyl; and $R_4$=H, glucosyl or 1,6-apiosyl.

Certain naturally occuring isoflavonoids of this invention of formula (I) have been isolated and identified in the prior art.

In a composition aspect, this invention relates to a pharmaceutical composition adapted for oral ingestion comprising, in admixture with a pharmaceutically acceptable, i.e., orally ingestible, carrier, an alcohol consumption inhibiting amount of an isoflavonoid of formula (I) in isolated, substantially pure form.

DETAILED DESCRIPTION OF THE PREFERRED EMBODIMENTS

Figure 1:
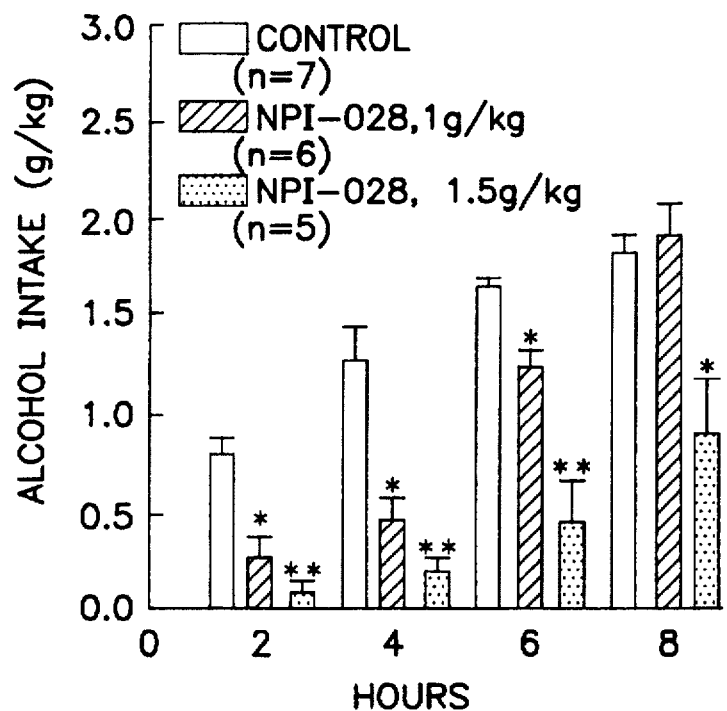
FIG. 1 is a bar graph which shows the the suppression of alcohol intake in alcohol-deprived P Rats by oral administration of NPI-028.

An unique structural feature of the class of compounds defined by formula (I) is the sugar moiety thereof attached at the C-8 ring carbon atom of the isoflavone ring system through a carbon-carbon bond linkage. This linkage is more resistant to enzymatic hydrolysis and metabolic activation than the carbon-oxygen linkage present in daidzin and daidzein and thus preserve for a longer period of time the pharmaceutical activity of the isoflavonoid and its conversion to an inactive metabolite or one having undesirable activity.

Examples of compounds of this invention within formula (I) include but are not limited to those wherein:

(a) $R_1$ is OH;

(b) $R_2$ is H, including those of (a);

(b) $R_3$ is H, OH or $OCH_3$, including those of (a) and (b); and (c) $R_4$ is OH, including those of (a), (b) and (c).

Examples of lower alkyl include but are not limited to methyl, ethyl, isopropoxy and n-butoxy.

Of the compounds of formula (I), puerarin ($R_1$ is OH and $R_2$, $R_3$ and $R_4$ are H) is especially preferred.

The compound or mixture of compounds of formula (I) are administered systemically, e.g., orally or by IM or IV injection, in admixture with a pharmaceutically acceptable carrier adapted for the route of administration. Oral administration is the preferred route and therefore the isoflavonoid(s) in the composition preferably is in admixture with an orally ingestible carrier and the composition preferably in the form of a tablet, dragee, capsule, caplet, pill or powder.

The individual doses generally will contain preferably 1.0 to 500 mg of one or more compounds of formula (I), the amount depending on the body weight of the individual, the route of administration and the number of doses administered daily and the response of the individual to the medication. The optimum dose can readily be determined by monitoring the amount of alcohol consumed by the individual while on the medication or, by the intensity of the individual's desire for alcohol, e.g., in clinical situations where alcohol is not accessible to the individual. In general, it is desirable for the dosage to the individual to be about 1.0 mg/kg to 120.0 mg/kg, preferably 2.0 mg/kg to 10.0 mg/kg, for a prolonged period, i.e., generally at least one week, preferably at least one month, and more preferably for as long as the individual cannot maintain sobriety without resorting to any medication.

Some of the isoflavonoids of formula (I) occur naturally, e.g., in Radix pueraria, Pueraria lobata and/or Citrus reticulata. Examples of their isolation therefrom substantially free from other isoflavonoids are described hereinafter. Others are isomers, homologues or analogues thereof which can be synthesized according to conventional methods known to those skilled in the art. For example, the synthesis of puerarin and its analogs can be accomplished by subjecting β-glucopyranosyl-2,6-dimethoxybenzene to a Friedel-Crafts acylation, followed by an Aldol condensation with p-methoxy-benzaldehyde, cyclization in the presence of thallium nitrate and demethylation with boron tribromide. Analogues thereof of formula (I) which lack and/or having a different substituent at one or more of the 3', 5 and 7 positions are produced in an analogous manner by substituting the appropriate β-glucopyranosyl-substituted benzene or benzaldehyde as reactants or by employing a different reaction scheme known in the art.

We established, in a 24-hr free-choice ethanol study using two different strains of alcohol-preferring rats, that the isoflavonoids in NPI-028 can significantly (~40%) suppress alcohol consumption. Furthermore, in a scheduled limited-access paradigm, NPI-028 produced a dose-dependent reduction in ethanol consumption. At 0.5 and 1.5 g/kg (i.p. injection), it reduced alcohol intake by 50% and 100%, respectively. In both experiments, food and water intakes were not affected (Overstreet et al., 1993). These studies clearly demonstrated that NPI-028 significantly reduced alcohol intake in two strains of alcohol-preferring rats under a range of conditions without the development of tolerance during a short course of treatment. It was also demonstrated that NPI-028 was effective in alcohol-preferring vervet monkeys. In summary, our present findings suggest that NPI-028 does not produce aversive effects. Rather, it may reduce the craving for alcohol centrally. The high doses (1-1.5 g/kg) needed to reduce alcohol intake are most likely due to the fact that NPI-028 is a mixture of plants which contain large amounts of inactive ingredients. Therefore, following this preliminary study, we conducted comprehensive fractionation studies on Pueraria lobata (one of the sources of the isoflavonoids present in NPI-028) to isolate in substantially pure form the active ingredients therein.

These fractionation studies yielded five isoflavonoids in isolated, substantially pure form, which collectively are solely or primarily responsible for the alcohol consumption suppressing activity of NPI-028. We determined that each of these isolated purified isoflavonoids, e.g., NPI-031G (puerarin), NPI-031D (daidzin), NPI-031E (daidzein), NPI-031K (mirificin), and NPI-031-F (3'-methoxypuerarin), were about 10 fold more active than crude NPI-028 in reducing alcohol consumption. For instance, NPI-031G (puerarin) at a dose of 150 mg/kg reduced alcohol intake in alcohol preferring rats.

One structural feature that the novel species of these active components of formula (I) have in common is that they all are a hydroxylated isoflavone with a glucose moiety attached at C-8 through a carbon-carbon covalent bond. We found that the compounds with a glucose moiety, such as NPI-031G (puerarin), are more potent than the corresponding aglycone. It is conceivable that the sugar moiety enhances the solubility of the compound and facilitates its absorption. We also found that the sugar moiety in NPI-031G (puerarin), its methoxy analog NPI-031-F (3'-methoxy-puerarin), its hydroxy analogue NPI-031H (3'-hydroxy-puerarin) and its apiosyl analogue NPI-031K (formula (I), $R_1$=OH; $R_1$=H,$R_3$=$CH_3$, and $R_4$=apiosyl(1-6)) is attached to the isoflavone through a carbon-carbon bond at C-8, which is more stable to enzymatic hydrolysis and metabolic degradation than a corresponding carbon-oxygen linkage, such as is present in diadzin. This is evidence that daidzin with a C-O linkage at C-7 tends to lose the glucose moiety under physiological condition and the resulting daidzein showed estrogenic activity because of its structural resemblance to estradiol. In contrast, NPI-031-G and its C-8 substituted analogs resist hydrolysis and show no estrogenic activity.

Recently, Keung and Vallee demonstrated that daidzin and daidzein were the active herbal components isolated from Radix pueraria that suppressed alcohol intake in Syrian Golden hamsters (Keung and Vallee, 1993a; 1993b; Keung et al., 1995) and in U.S. Pat. No. 5,204,369, they claim using diadzin as a selective inhibitor of ALDH-1 for the treatment of alcohol dependence. These compounds are also two of the five active isoflavonoids isolated by us from *Pueraria lobata*.

Daidzin and daidzein differ from the compounds of this invention of Formula (I) by being unsubstituted at the 8 position and having a carbon-oxygen linked β-D-glucose moiety at C-7 position. Daidzin differs from disulfiram in its selective and reversible inhibition of ALDH-1 (Keung and Vallee, 1993a). Daidzin also decreases blood alcohol levels and shortens sleep time induced by ethanol (Xie et al., 1994). Daidzin and its aglycone daidzein are potent human ALDH-1 inhibitors (Keung et al., 1993a,b) and suppress ethanol consumption in Syrian golden hamster (Keung et al., 1995). ALDH inhibitors are anti-dipsotropic in most animal models. The aversive effects produced by acetaldehyde accumulation resulting from ALDH inhibition has attracted considerable attention ever since disulfiram was introduced 50 years ago as a therapeutic agent. However, disulfiram was ineffective in several recent clinical trials; furthermore, it covalently modifies the essential enzyme through a sulfhydryl group.

Daidzin and daidzein are naturally occurring compounds and potent reversible ALDH inhibitors. However, Keung and Valle recently reported (Keung et al., 1995) that daidzin does not affect overall acetaldehyde metabolism in hamster. In other words, daidzin-sensitive mitochondrial ALDH is not the only enzyme that is essential for acetaldehyde metabolism in hamster. This report is in disagreement with U.S. Pat. No. 5,204,369 which issued to Keung and Vallee. It is conceivable that the observed suppressant effect of daidzin on alcohol intake in hamster may work through a mechanism that differs than inhibition of ALDH receptor.

Source and Botanical Identification of Chinese Herbal Plants

For over two thousand years, Chinese herbalists have known of the medicinal value of Ge Gen (Japanese kudzu, English *Pueraria Lobata*). In the *Handbook of Prescriptions for Emergency Treatments* of 340 AD, the plant including flower was prescribed as a treatment for alcohol intoxication. A number of herbal remedies containing *Pueraria Lobata* are still commonly used in China to dispel drunkenness. Its use to reduce alcohol consumption was never reported.

*Pueraria lobata* (Ge Gen) was purchased and identified by a botanist at Shenyang College of Pharmacy in China. A vigorous botanical identification of the herbal plant starting materials is essential for future collection and large scale preparation. *Pueraria lobata* was subjected to comprehensive fractionation employing a powerful high speed countercurrent chromatography technique which allows effective purification of polar natural products such as glycosides and water soluble components. Of the five isoflavonoids shown in Chart A below, four of which are compounds defined by formula (I).

Chart A: Chemical Structures of Purified Herbal Components

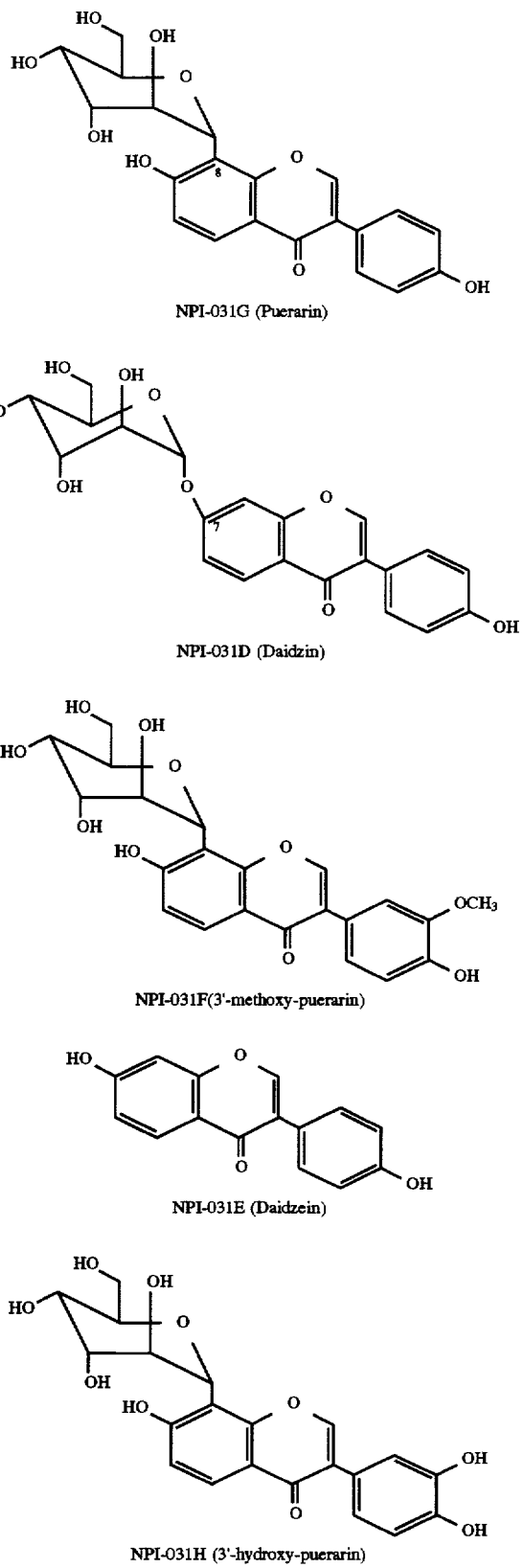

NPI-031G (Puerarin)

NPI-031D (Daidzin)

NPI-031F(3'-methoxy-puerarin)

NPI-031E (Daidzein)

NPI-031H (3'-hydroxy-puerarin)

-continued
Chart A: Chemical Structures of Purified Herbal Components

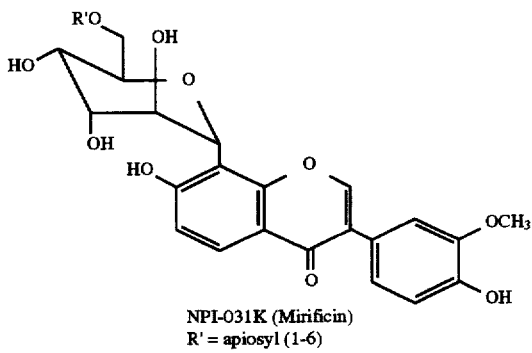

NPI-031K (Mirificin)
R' = apiosyl (1-6)

According to our animal data, puerarin is slightly less active than daidzin in suppressing alcohol intake on a molar basis. However, it is not an ALDH inhibitor (Keung et al., 1993a,b). In addition, puerarin is not a phystoestrogen. Therefore, puerarin is a much safer compound with a better therapeutic index than daidzin or daidzein as a potential agent for the treatment of alcohol dependence. Furthermore, its analogs such as 3'-methoxy (NPI-031F) showed better alcohol consumption suppressant effects than NPI-031-G (puerarin).

From the foregoing description, one skilled in the art can easily ascertain the essential characteristics of this invention and, without departing from the spirit and scope thereof, can make various changes and modifications of the invention to adapt it to various usages and conditions. The entire disclosures of all applications, patents and publications cited herein are incorporated herein by reference. The following preferred specific embodiments are, therefore, to be construed as merely illustrative and not limitative of the scope of the invention whatsoever. In the following examples, all temperatures are set forth uncorrected in degrees Celsius and, unless otherwise indicated, all parts and percentages are by weight.

EXAMPLE 1

Fractionation of *Pueraria lobata*

Following the fractionation scheme, 1.0 kg of the dry root of *Pueraria lobata* was ground into powder (16 mesh in size). The powderous material was partitioned between ether and water to remove fat and non-polar substances. The aqueous layer was then extracted with n-butanol three times (3.0L). The combined n-butanol extract was concentrated under reduced pressure to give 350 g of gummy material. Normal phase silica gel column chromatography using a $CH_2Cl_2$/MeOH (80:20) solvent system provided 172 fractions. Fractions 49 to 68 were combined and recrystallized from MeOH to give daidzein (NPI-031E) and genistein (NPI-031L). Fractions 33 to 48 and 69 to 109 were combined to give 36.4 g of semipurified extract. Fractions 110 to 172 were combined to give 13 g of semipurified extract. Repeated silica gel column chromatography of the combined fraction 33–109 using a $CH_2Cl_2$/MeOH (85:15) solvent system gave a major component from fraction 21 to 99 with a total weight of 19.89 g. This fraction was combined with previous fraction 89–109 (10.8 g) and subjected to high speed countercurrent chromatography ( Ito's planetary system; Lee et al., 1989) using a two-phase solvent system (n-butanol:t-butyl methyl ether:$CH_3CN$:$H_2O$/2:2:1:5). The lower phase was used as the mobile phase and eluted at a flow rate of 3.0 mL/min to give three purified fractions: daidzin (NPI-031D 1.8 g), puerarin (NPI-031G, 16.7 g), and methoxy-purearin (NPI-031F, 0.16 g). The combined fraction 110–172 (7.8 g) derived from previous silica gel column chromatography was further purified by the high speed countercurrent chromatography method using a two-phase solvent system (n-butanol:t-butyl methyl ether: $CH_3CN$:$H_2O$/2:2:1:5) and the same conditions employed before. Fractions 17 to 23, eluted from high speed countercurrent chromatography, were combined to give 3.62 g of enriched intermediate, which was further purified by the high speed countercurrent chromatography method to give as additional compounds 3'-hydroxy-puerarin (NPI-031H) and mirificin (NPI-031-31K).

Chemical Characterization of Purified Compounds

The purified herbal components derived as described in above were subjected to a series of standard chemical and physical measurements including melting point, elemental analysis, UV, IR and NMR (both $^1$H and $^{13}$C). The chemical and physical data obtained for each compound were compared with the literature values for known compounds. We have isolated a total of 5 compounds from *Pueraria lobata*. Chemical structures of these compounds were established on the basis of their respective chemical, physical and spectroscopic data.

EXAMPLE 2

NPI-031G: Puerarin 8-β-D-glucopyranosyl -7- Hydroxy-3[4-hydroxyphenyl]-1-benzopyran-4-one, or (8-β-D-Glucopyranosyl-4'-7- Dihydroxyisoflavone)

NPI-031G was obtained as white crystals, m.p.187°–189° C. IR $(KBr)_{cm}^{-1}$: 3410 (OH), 1630 (conjugated C=O), 1517 (C=C). EI/MS showed molecular ion peak at 416 [M$^+$], which together with $^{13}$C-NMR data suggested the molecular formula as $C_{21}H_{20}O_9$. The $^1$H and $^{13}$C-NMR data of C-1" in the sugar region suggested a characteristic β-D-glucopyranoside structure. The β configuration at the anomeric center of the D-glucopyranosyl moiety was suggested by the chemical shift (δ=4.82), the large $J_{1,2}$ coupling of anomeric proton (9.7 Hz) and its $^{13}$C-NMR data. This was in agreement with the finding that alkaline hydrolysis of NPI-031G failed to afford the sugar and aglycone.

By comparison of the data with literature values (Yasuda et al., 1995 ), it was concluded that the structure of NPI-031G is 8-β-D-Glucopyranosyl-4'-7-Dihydroxyisoflavone (Puerarin). NPI-031G: $^1$H-NMR (250 MHz, DMSO-$d_6$) δ: 9.56 (s, OH), 8.40 (1H, s, H-2), 7.95 (1H, d, J=8.81 Hz, H-5), 7.41 (2H, d, J=8.60 Hz, H-2' and H-6'), 7.00 (1H, d, J=8.81 Hz, H-6), 6.81 (2H, d, J=8.60 Hz, H-3' and H-5'), 4.82 (1H,d, J=9.7 Hz, H-1"); $^{13}$C-NMR (62.5 MHz, DMSO-$d_6$) δ: 174.93 (C-4), 161.07 (C-7), 157.12 (C-4'), 156.0 (C-9), 152.67 (C-2), 130.03 (C-2' and C-6'), 126.26 (C-5), 123.06 (C-1'), 122.05 (C-3), 116.8 (C-10), 114.97 (C-3' and C-5'), 114.96 (C-6), 112.61 (C-8), 81.79 (C-5"), 78.71 (C-3"), 73.39 (C-1"), 70.75 (C-2"), 70.70 (C-4"), 61.5 (C-6").

EXAMPLE 3

_NPI-031D: Daidzin (7-O-β-D-Glucopyranosyl-4', 7-Dihydroxyisoflavone)

NPI-031D was obtained as white needles, m.p. 235°–237° C. FAB/MS showed molecular ion at 416 [M$^+$] which together with $^{13}$C-NMR data suggested molecualr formula as $C_{21}H_{20}O_9$. Acid hydrolysis provided glucose and corresponding aglycone (daidzein). The chemical structure of NPI-031D was confirmed by comparison of its $^1$H-NMR and $^{13}$C-NMR data with reported literature values). NPI-031D: $^1$H-NMR (250 MHz, DMSO-$d_6$) δ: 9.58 (s, OH), 8.40 (1H,s, H-2), 8.05 (1H, d, J=8.79 Hz, H-5), 7.41 (2H, d, J=8.60 Hz, H-2' and H-6'), 7.24 (1H, d, J=2.20 Hz, H-8), 7.15 (1H, dd, J=2.2 and 8.79 Hz, H-6), 6.82 (2H, d, J=8.60 Hz, H-3' and H-5'), 4.68 (1H, d, J=5.30 Hz, H-1"); $^{13}$C-NMR (62.5 MHz, DMSO-$d_6$) δ: 174.75 (C-4), 161.37 (C-7), 157.24 (C-9), 157.02 (C-4'), 153.33 (C-2), 130.08 (C-2' and C-6'), 126.96 (C-5), 123.68 (C-1'), 122.29 (C-3), 118.44 (C-10), 115.58 (C-6), 114.96 (C-3' and C-5'), 103.36 (C-8), 99.94 (C-1"), 77.18 (C-5"), 76.45 (C-3"), 73.11 (C-2"), 69.6 (C-4"), 60.61 (C-6").

EXAMPLE 4

_NPI-031E: Daidzein (4',7-Dihydroxyisoflavone)

NPI-031E was obtained by acid hydrolysis of daidzin. NPI-031E: $^1$H-NMR (250 MHz, DMSO-$d_6$) δ: 9.50 (s, OH), 8.41 (1H, s, H-2), 7.95(1H, d, J=8.80 Hz, H-5), 7.41(2H, d, J=8.60 Hz, H-2' and H-6'), 7.39 (1H, d, J=2.20 Hz, H-8), 7.30 (1H, dd, J=2.20 and 8.80 Hz), 6.82 (2H, d, J=8.60 Hz, H-3' and H-5'); $^{13}$C-NMR (62.5 MHz, DMSO-$d_6$) δ: 174.5 (C-4), 162.60 (C-7), 157.61 (C-9), 157.32 (C-4'), 152.20 (C-2), 129.94 (C-2' and C-6'), 127.11 (C-5), 123.90 (C-1'), 122.59 (C-3), 116.78 (C-10), 115.10 (C-6), 114.90 (C-3' and C-5'), 102.10 (C-8).

EXAMPLE 5

NPI-031F: 3'-Methoxy-Puerarin ( 8-C-β-D-Glucopyranosyl-3'-Methoxy-4',7-Dihydroxy-isoflavone)

NPI-031F was obtained as white powder. FAB/MS showed molecular ion at 446 [M$^+$], which together with $^{13}$C-NMR data suggested the molecular formula as $C_{22}H_{22}O_{10}$. The position of the 3'-methoxy group was determined by NOE study. A strong NOE effect was observed between the methoxy methyl and its adjacent aromatic 2'-H. Together with $^{13}$C-NMR data, it was established that the structure of NPI-031-F is 3'-methoxy-puerarin. NPI-031F: $^1$H-NMR (250 MHz, DMSO-$d_6$) δ: 9.11 (s,OH),8.41 (1H,s,H-2), 7.95(1H, d, J=8.82 Hz, H-5), 7.17 (1H, d, J=1.90 Hz, H-2'), 7.04 (1H, dd, J=8.18 and 1.90 Hz, H-6'), 7.00 (1H, d, J=8.82 Hz, H-6), 6.81 (1H, d, J=8.18 Hz, H-5'), 4.82 (1H, d, J=9.7 Hz, H-1"), 3.80 (3H, s, OCH$_3$); $^{13}$C-NMR (62.5 Mhz, DMSO-$d_6$) δ: 174.87 (C-4), 161.07 (C-7), 156.0 (C-9), 152.93 (C-2), 147.16 (C-3'), 146.37 (C-4'), 126.26 (C-5), 123.01 (C-1'), 122.94 (C-3), 121.49 (C-6'), 117.0 ( C-10), 115.15 (C-6 and C-5'), 112.97 (C-2'), 112.61 (C-8), 81.79 (C-3"), 78.76 (C-5"), 73.41 (C-1"), 70.75 (C-2"), 70.70 (C-4"), 61.5 (C-6"), 55.60 (OCH$_3$).

EXAMPLE 6

NPI-031H: 3'-Hydroxy-Puerarin (8-β-D-Glucopyranosyl-3',4',7-Trihydroxy-isoflavone)

NPI-031H was obtained as white powder. FAB/MS showed molecular ion at 432 [M$^+$], which together with $^{13}$C-NMR data suggested the molecular formula as $C_{21}H_{20}O_{10}$. Based on the analyses of its $^1$H-NMR and $^{13}$C-NMR data, it was established that the structure of NPI-031H is the 3'-hydroxy-puerarin. $^1$H-NMR (250 MHz, DMSO-$d_6$) δ: 8.98 (s, OH), 8.29 (1H, s, H-2), 7.93 (1H, d, J=8.82 Hz, H-5), 7.02 (1H, d, J=1.90 Hz, H-2'), 6.98 (1H, d, J=8.82 Hz, H-6), 6.80 (1H, dd, J=8.15 Hz and 1.90 Hz, H-6'), 6.75 (1H, d, J=8.15 Hz, H-5'), 4.80 (1H, d, J=9.7 Hz, H-1"); $^{13}$C-NMR (62.5 MHz, DMSO-$d_6$) δ: 174.90 (C-4), 161.04 (C-7), 156.0 (C-9), 152.61 (C-2), 145.23 (C-4'), 144.74 (C-3'), 126.32 (C-5), 123.22 (C-1'), 122.97 (C-3), 119.78 (C-6'), 116.80 (C-10), 116.60 (C-5'), 115.32 (C-2'), 115.0 (C-6),112.58 (C-8), 81.79 (C-5"), 78.78 (C-3"), 73.42 (C-1"), 70.76 (C-2"), 70.70 (C-4"), 61.50 (C-6").

EXAMPLE 7

NPI-031K: Daidzein-8-C-Apiosyl (1–6)

NPI-031K was obtained as white powder. HPLC analysis indicated that this fraction was about 90% pure. Because of the impurities present in the sample, it was not possible to obtain molecular ion information from EI-MS. However, based on its $^1$H-NMR and $^{13}$C-NMR data, a tentatively structure shown in Chart A was proposed. The linkage for the second sugar unit was established as apiosyl (1, d, J=8.82 Hz, H-6), 6.81 (2H, d, J=8.60 Hz, H-3' and H-5'), 4.78 (2H, m, H-1" and H-1'"); $^{13}$C-NMR (62.5 MHz, DMSO-$d_6$) δ: 174.92 (C-4), 161.03 (C-7), 157.12 (C-4'), 156.0 (C-9), 152.64 (C-2), 130.04 (C-2' and C-6'), 126.29 (C-5), 123.09 (C-1'), 122.51 (C-3), 116.8 (C-10), 114.96 (C-6 or C-3' and C-5'), 112.48 (C-8), 109.00 (C-1'"), 80.04 (C-5"), 78.75 (C-3'"), 78.74 (C-3"), 75.63 (C-2'"), 73.20 (C-1"), 73.18 (C-4'"), 70.52 (C-2"), 70.50 (C-4"), 68.1 (C-6"), 62.8 (C-5'").

EXAMPLE 8

NPI-031L: Genistein (4',5,7-Trihydroxyisoflavone)

NPI-NPI-031L was obtained as colorless needles, m.p. 212°–214° C. $^1$H-NMR (250 MHz, DMSO-$d_6$) δ: 8.33 (1H, s, H-2), 7.36 (2H,d, J=8.1 Hz, H-2'), 6.79 (2H, d, J=8.1 Hz, H-3'), 6.66 (1H, d, J=2.0 Hz, H-8), 6.43 (1H, d, J=2.0 Hz, H-6); $^{13}$C-NMR (62.5 MHz, DMSO-$d_6$) δ: 180.4 (C-4), 162.5 (C-7),161.0 (C-5), 157.2 (C-4'), 157.0 (C-9),154.2 (C-2), 130.1 (C-2'),122.6 (C-3), 121.1 (C-1'), 115.1 (C-3'), 106.0 (C-10), 99.6 (C-6), 94.6 (C-8).

Animal Studies

Suppressant Effects of NPI-028 on Alcohol Intake

EXAMPLE 9

Alcohol Preferring P Rats

After stable levels of alcohol intake were attained (Rezvani et al., 1995a), the rats (n=8) received i.p. injections of either distilled water (0 mg/kg) or three doses of NPI-028 at 9:30 a.m. NPI-028 1 g/kg was also tested p.o. Intakes of alcohol, water, food, and total fluid, as well as alcohol preference, were recorded 24 hr after injection (Table 1).

TABLE 1

Effects of NPI-028 on Alcohol Intake and Preference in P Rats at 24 hr

| Parameters | Dose of NPI-028 (g/kg, i.p.) | | | | |
|---|---|---|---|---|---|
| | 0.0 | 0.25 | 0.5 | 1.0 | 1.0 g/kg, p.o. |
| Alcohol Intake (g/kg/day) | 5.9 ± 0.6 | 5.4 ± 0.6 | 4.6 ± 0.7* | 2.9 ± 1.0*,+ | 5.0 ± 0.5 (−25%) |
| Water Intake (g/kg/day) | 1.6 ± 0.4 | 1.4 ± 0.5 | 1.9 ± 0.7 | 1.6 ± 0.5 | 1.7 ± 0.4 (+4%) |
| Food Intake (g/kg/day) | 64 ± 3.0 | 45 ± 2.0* | 49 ± 4.0* | 26 ± 3.0*,+ | 46 ± 2.0 (−2%) |
| Total Fluid Intake (ml/kg/day) | 91 ± 4.0 | 83 ± 4.0 | 79 ± 5.0* | 53 ± 9.0*,+ | 81 ± 7.0 (−18%) |
| Alcohol Preference ([Alc/Alc + water]100) | 82 ± 4.0 | 82 ± 7.0 | 72 ± 8.0 | 60 ± 11* | 89 ± 4.0 (−4%) |

*Significantly different from control (0.0), $p < 0.05$.
+Significantly different from 0.50 g/kg, $p < 0.05$.

Results: Although there was clearly a dose-dependent decrease in alcohol intake in this sample of P rats, there was also a dose-dependent reduction in food intake. The reduction in food intake was not seen in our preliminary studies and underlines the possibility that NPI-028 is not a crude substance, the relative proportions of the constituent plants was fiber.

Even so, however, Table 1 shows that NPI-028 is also orally active at the 1.0 g/kg dose with a good degree of selectivity. Because humans are most likely to take NPI-028 orally, it is possible that there would be some selectivity in them as well.

EXAMPLE 10

Alcohol-Deprived P Rats

One common feature rodents which voluntarily drink substantial amounts of alcohol is the "alcohol deprivation effect", the tendency to elevate drinking above baseline values when deprived of the opportunity to drink alcohol (Rezvani et al., 1992; Sinclair et al., 1989). The present study took advantage of this phenomenon to characterize further the effects of NPI-028 on alcohol intake. After establishment of a stable baseline for alcohol and water intake, the alcohol tube was removed from each cage for 17 hr (5:00 p.m.-10:00 a.m.). This deprivation schedule was employed to stimulate alcohol intake in P rats and detect the potential anti-craving effect of NPI-028. Previous workers have indicated that P and FH rats will increase their alcohol intake after a period of alcohol deprivation (Rezvani et al., 1992). At 9:00 a.m. on the day after the alcohol tube was removed, P rats were given NPI-028 1.0 or 1.5 g/kg p.o. or an equal volume of control vehicle (3 ml distilled water), and 1 hr later the alcohol tube was returned to their cage with food and water available ad lib. Alcohol and water intakes were measured every two hr up to 8 hr and at 24 hr. Food intake was measured at 8 and 24 hr. The results are shown in FIG. 1, which is a bar graph showing the effect of oral administration of NPI-028 iin suppressing alcohol intake in alcohol-deprived P rats. (Mean±S.E.M., *p<0.02, **p<0.01 from control).

Compared with control vehicle, NPI-028 1.0 and 1.5 g/kg significantly reduced alcohol intake (FIG. 1). FIG. 1 illustrates the time course of the effect of NPI-028. Alcohol intake was significantly suppressed in a dose-dependent manner for more than six hr. The alcohol intake of rats which received 1.5 g/kg NPI-028 remained significantly (p<0.01) suppressed even after 24 hr (4.3±0.7 g/kg in NPI-treated group vs. 6.2±0.3 g/kg in the control group).

Table 2 shows that NPI-028 did not change food and water intake at 8 and 24 hr after the treatment.

| Treatment | n | Food Intake (g/kg) | | Water Intake (g/kg) | |
|---|---|---|---|---|---|
| | | 8 hr | 24 hr | 8 hr | 24 hr |
| Control | 7 | 10 ± 7 | 27 ± 2.0 | 2.0 ± 1.0 | 2.6 ± 1.0 |
| NPI-028 | | | | | |
| 1.0 g/kg | 6 | 10 ± 1 | 26 ± 0.6 | 0.8 ± 0.6 | 1.4 ± 0.5 |
| 1.5 g/kg | 5 | 10 ± 1 | 26 ± 2.0 | 1.0 ± 0.9 | 4.0 ± 1.8 |

EXAMPLE 11

Alcohol-Deprived FH Rats

The anti-craving effect found in Experiment B was confirmed in another strain of alcohol preferring rat. Eight adult male FH rats with intakes of 5 g/kg/day alcohol in a two-bottle choice paradigm were deprived of alcohol for exactly 24 hr on two separate occasions approximately 3 weeks apart; food and water were continuously available. On one occasion, the alcohol was returned and readings were taken 24 hr later; there was a significant 30% increase in alcohol intake. On the other occasion, NPI-028 0.75 g/kg was injected i.p. one hr before the alcohol was returned and readings were taken again 24 hr later. NPI-028 completely abolished the 30% increase (2.18 g/kg) in alcohol intake seen in the alcohol-deprived FH rats; instead, there was a 25% (1.49 g/kg) decrease in alcohol intake in the NPI-028-treated rats (t=4.86, p<0.01).

EXAMPLE 12

FH Rats Maintained on Limited Scheduled Access

Figure 2:
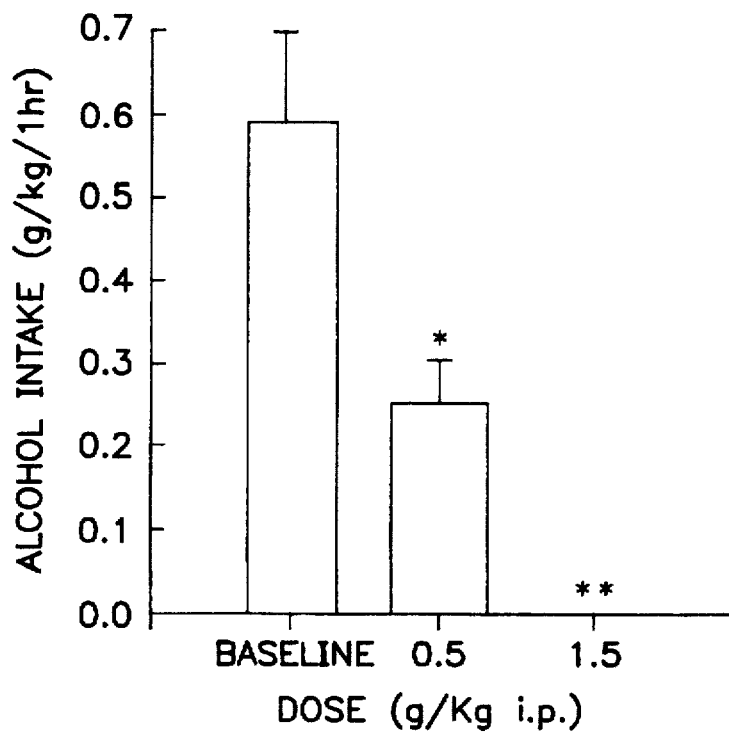
FIG. 2 is a bar graph which shows the suppression of alcohol intake in FH Rats on scheduled access thereto by oral administration of NPI-028.

The 8 male adult FH rats in this experiment had been used previously in a scheduled access paradigm in order to test the effects of short-acting drugs on alcohol intake. The rats had continuous access to food and water, but access to alcohol was limited to only 1 hr/day, from 10:00 a.m. to 11:00 a.m. NPI-028 0.5 and 1.5 g/kg of and control vehicle (0.0) were injected 15–20 min prior to alcohol exposure at weekly intervals. Alcohol and food intake were measured 1 hour after alcohol exposure. Our results, shown in bar graph form in FIG. 2, show that NPI-028 suppressed alcohol intake in FH Rats maintained on scheduled access. (Mean±S.E.M.). *p<0.01, **p<0.001, n=8. (0.5 mg/kg reduced intake by half and 1.5 mg/kg abolished intake).

EXAMPLE 13

Sub-Chronic I.P. Administration in FH Rats

Repeated injections of most anti-craving drugs, including the newly approved naltrexone, leads to tolerance in animals. NPI-028 was tested sub-chronically in 8 male FH rats. After establishment of stable baselines for alcohol and water intake, an intermediate dose of 0.75 g/kg was given i.p. at 9:30 a.m. on 4 consecutive days, and alcohol, food and water intake were recorded 24 hr after each injection.

Figure 3:
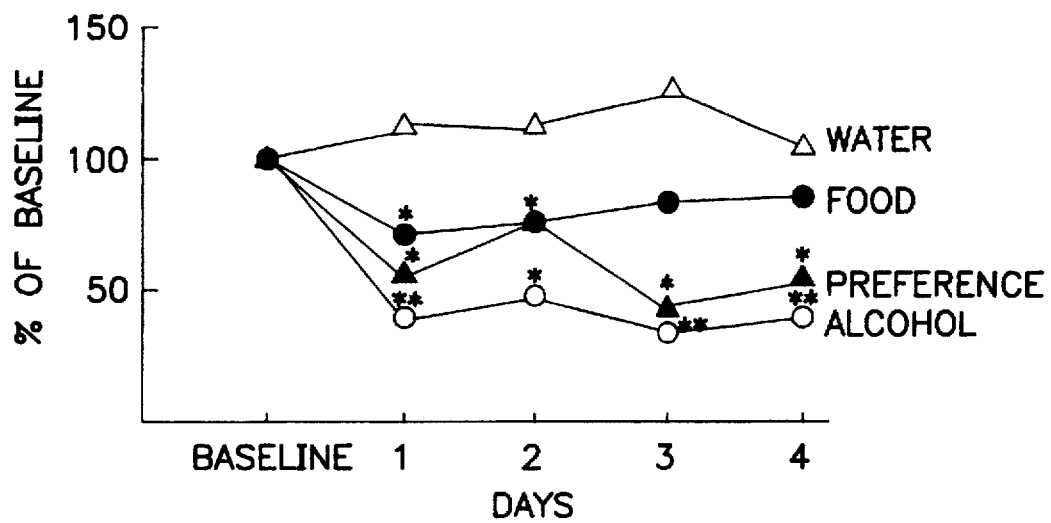
FIG. 3 is a graph which shows the suppression of alcohol intake and preference in FH Rats after i.p. administration of NPI-028.

Results: After the first administration, ethanol intake was reduced by 40% (FIG. 1); food intake was reduced by 15% significantly less than the reduction of alcohol intake. When 0.75 g/kg was administered for 4 consecutive days, there was no evidence of tolerance to its alcohol intake-reducing effect. However, there was tolerance to the effect on food intake, which returned to the baseline on Days 3 and 4. There was a trend toward an increase in water intake in the NPI-028 rats. The increase in water intake, combined with attenuation of alcohol intake, produced a significant reduction (up to 50%) in alcohol preference is shown in graph from in FIG. 3, which shows that sub-chronic administration of NPI-028 (0.75 g/kg, i.p.) suppressed alcohol intake and preference in FH Rats (p<0.02 and **p<0.01; n=8).

EXAMPLE 14

Taste Aversion in Sprague-Dawley Rats

Figure 4:
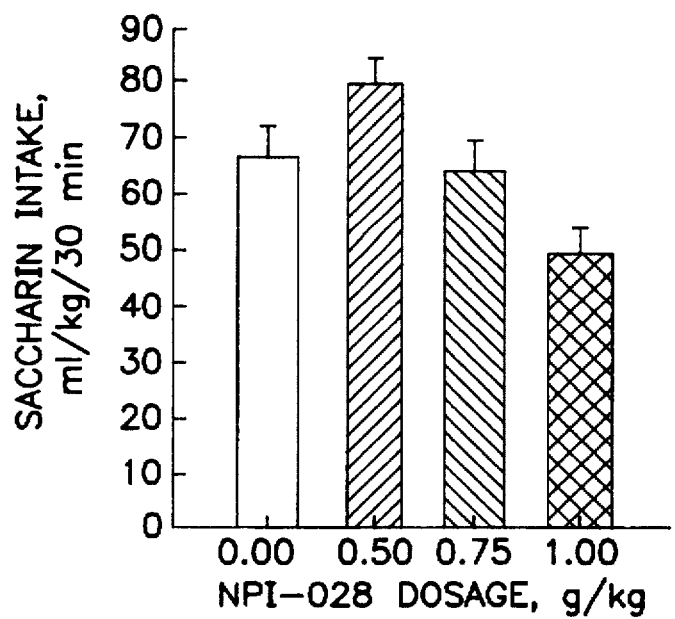
FIG. 4 is a bar graph which shows that NPI-028 did not induce taste aversion to saccharine in alcohol naive rats.

Occasional reports have suggested that certain drugs, including even naltrexone, may be suppressing alcohol intake by producing a taste aversion. The potential for NPI-028 to produce taste aversion was tested in Sprague-Dawley rats by pairing the injections of vehicle or NPI-028 with exposure to the novel taste of a solution of saccharin. Seventeen-hr water-deprived rats were given 30 min access to a solution of 0.1% saccharin and then injected with one of the doses (0.5, 0.75 or 1.5 g/kg i.p.) of NPI-028 or control vehicle (0.00). On Day 2, they received 1 hr access to water but no injection. On Day 3, they were treated as on Day 1, and on Day 4 as Day 2. On day 5, they were given 30 min access to saccharin, and intakes were measured. As illustrated in bar graph form in FIG. 4, NPI-028 did not induce taste aversion to sachcharin in alcohol naive rats (N=8 in each group) and thus did not alter the intake of saccharin. Therefore, there was no evidence for taste aversion.

EXAMPLE 15

Blood Alcohol Level in P rats

For any compound which reduces alcohol consumption, it is crucial to know if the effect is peripheral or central. If a compound inhibits alcohol metabolism in the system for any reason it is likely that the animal will reduce its alcohol consumption to avoid alcohol buildup beyond a certain limit. On the other hand, if a compound accelerates alcohol metabolism, the animal may drink more alcohol to meet its pharmacological/physiological need. The same argument is true about the toxic metabolite of ethanol, acetaldehyde. It is obvious that a compound with disulfiram-like effects will not be desirable simply because of buildup of acetaldehyde in the body, which leads to very unpleasant side effects. For these reasons, an experiment was carried out to determine the effect of NPI-028 on alcohol metabolism in alcohol-naive P rats. Rats were injected i.p. with either control vehicle or NPI-028 1.0 g/kg and 20 min later with ethanol (2.5 g/kg, 16% v/v). Blood alcohol concentrations were measured by gas chromatography at 1, 3 and 5 hours after ethanol administration (Rezvani et al., 1992).

Figure 5:
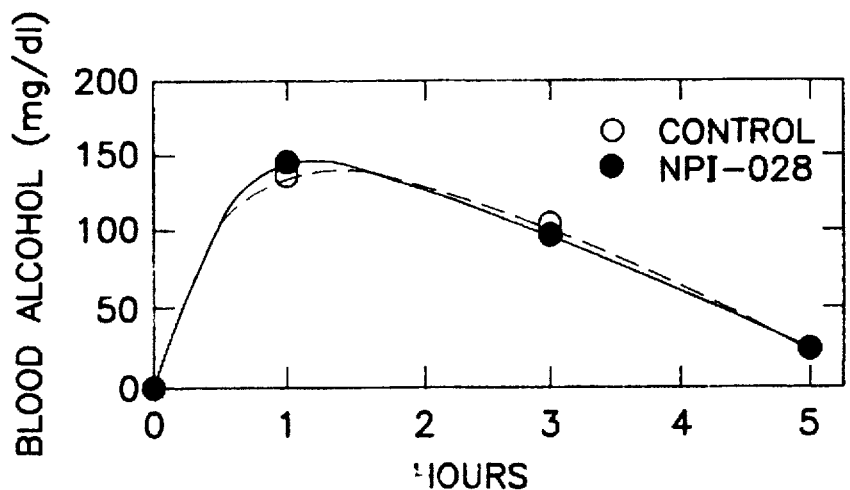
FIG. 5 is a graph which shows that NPI-028 does not affect blood alcohol concentration.

Results: As shown in the graph of FIG. 5, acute NPI-028 did not affect blood alcohol concentration.

EXAMPLE 16

Alcohol-Preferring Vervet Monkeys

Our initial findings in P and FH rats was extended to African green vervet monkeys that also voluntarily consume large amounts of alcohol in a free choice two-bottle paradigm (Rezvani et al., 1996). The 6 male alcohol-preferring monkeys had baseline consumptions of alcohol up to 3.6 g/kg/day or about 2.5 g/kg in a 6-hr session. After establishment of a stable baseline for a solution of 7.5% (v/v) alcohol, monkeys were injected i.p. with either vehicle or NPI-028 (0.18, 0.37 or 0.75 g/kg in a volume of 3 ml/monkey) at 10:00 a.m., with at least 1 week interval between consecutive injections. Alcohol and water intake were measured at 2, 4, 6, and 24 hr after injection.

Figure 6:
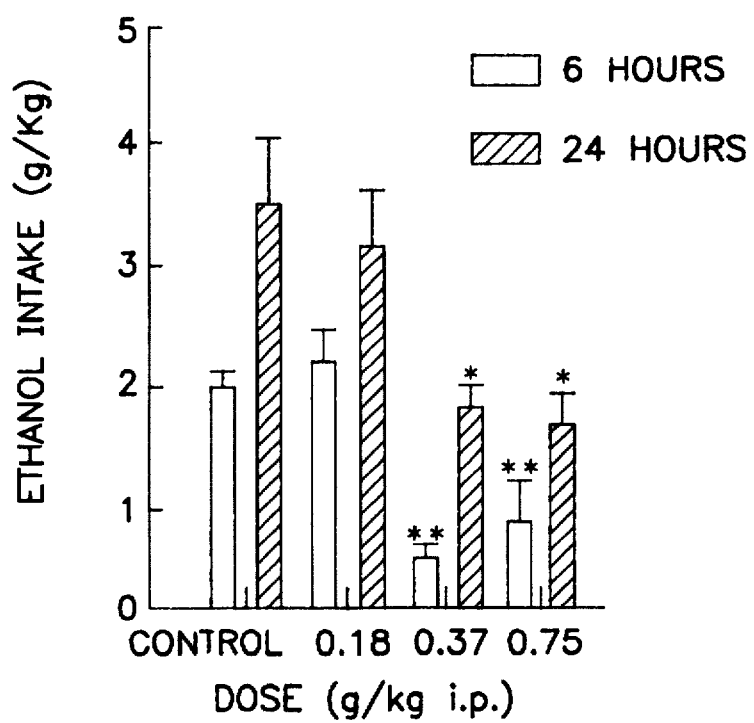
FIG. 6 is a bar graph which shows that NPI-028 reduced alcohol intake in monkeys.

Results: As shown in bar graph form in FIG. 6, NPI-028 reduced alcohol intake in monkeys (Mean±S.E.M., *p<0.05, **p<0.02, n=6) and produced a significant dose-dependent reduction in alcohol intake at 6 and 24 hours. There was a nonsignificant trend toward an increase in water intake, but variability was large. The cage design did not allow food intake to be accurately measured; however, none of the subjects gained or lost a significant amount of body weight.

Suppressant Effects of Purified Components of NPI-028 on Alcohol Intake

EXAMPLE 17

NPI-031-G (Puerarin) in P Rats.

Puerarin is an isoflavone-C-glycoside and the major component of the *Pueraria Lobata*. Preliminary studies showed puerarin 100 mg/kg to be selectively active in suppressing alcohol intake (see enclosed manuscript). After establishment of stable baselines for a solution of 10% (v/v) alcohol intake, P rats were injected i.p. with vehicle (0.0) or puerarin 50, 100, or 150 mg/kg, or 100 mg/kg p.o. at 9:30 a.m. in a cross-over design. At least 3 days was allowed between injections. Intake of alcohol, water, food, and total fluid, and alcohol preference, were recorded 24 hr after each treatment. The results are shown in Table 3.

TABLE 3

Effects of NPI-031G on Alcohol Intake and Preference in P rats

| Parameter | Dose (mg/kg, i.p.) | | | | |
|---|---|---|---|---|---|
| | 0.0 | 50 | 100 | 150 | 100 mg/kg. p.o. |
| Alcohol Intake (g/kg/day) | 6.2 ± 0.3 | 5.4 ± 0.4 | 4.8 ± 0.4* | 4.6 ± 0.5** | 4.7 ± 0.7 (−39) |
| Water Intake (g/kg/day) | 1.0 ± 0.4 | 7.0 ± 0.2 | 2.8 ± 0.3 | 7.0 ± 3.0 | 11 ± 4.0 (+69) |
| Food Intake (g/kg/day) | 57 ± 2.0 | 52 ± 2.0 | 49 ± 4.0 | 49 ± 3.0 | 41 ± 3.0 (−13) |
| Total Fluid Intake (ml/kg/day) | 83 ± 3.0 | 72 ± 5.0 | 68 ± 4.0 | 63 ± 5.0 | 75 ± 7 (−27) |
| Alcohol Preference | 91 ± 3.0 | 90 ± 4.0 | 88 ± 6.0 | 88 ± 5.0 | 74 ± 8 (−18) |

Results: NPI-031G (Puerarin) dose-dependently reduced alcohol intake in P rats without much effect on food intake. Note that puerarin, like NPI-028, is active orally and is fairly selective.

EXAMPLE 18

NPI-031-G (Puerarin) on Alcohol Intake in HAD Rats.

When High Alcohol Drinking (HAD) rats became available for testing, we deciding to compare the effects of NPI-031G on them and P rats with the effects of naltrexone. The results are summarized in Table 4.

TABLE 4

Effects of NPI-031G on Intake and Preference

| | NPI-031G (150 mg/kg) | | | |
|---|---|---|---|---|
| | P Rats | | HAD Rats | |
| | Base | Drug | Base | Drug |
| Food Intake (g/kg) | 57 ± 2 | 49 ± 3 | 41 ± 1 | 40 ± 2 |
| Water Intake (ml/kg) | 1 ± 0.4 | 7 ± 3 | 16 ± 4 | 26 ± 5 |
| Alcohol Intake (g/kg) | 6.2 ± 0.3 | 4.6 ± 0.5* | 10.8 ± 0.7 | 8.1 ± 0.7* |
| Total Fluid Intake (ml/kg) | 83 ± 3 | 63 ± 5 | 150 ± 7 | 128 ± 6* |
| Alcohol Preference ([Alc/Alc + water]100) | 91 ± 5 | 88 ± 5 | 89 ± 3 | 80 ± 5 |

*Significantly different from baseline, p < 0.05.

TABLE 5

Effects of Naltrexone on Alcohol Intake

| | Naltrexone (30 mg/kg) | | | |
|---|---|---|---|---|
| | P Rats | | HAD Rats | |
| | Base | Drug | Base | Drug |
| Alcohol Intake | 7.4 ± 5 | 4.7 ± 0.6* | 10.3 ± 1.2 | 8.5 ± 1.0 |

*Significantly different from baseline, p < 0.05

The data in Table 5 above indicates that NPI-031G has relatively similar effects (approximately 25% suppression) on alcohol intake in both P and HAD rats, without much affect on the other parameters. Total fluid intake tends to be decreased because the decrease in alcohol intake is not made up by a compensatory increase in water intake. In contrast to the similar effects of NPI-031G in P and HAD rats, Table 5 shows that naltrexone has a much less inhibitory effect on alcohol intake in the HAD rats (−17%) compared to the P rats (−37%). We have found the HAD rats to be less sensitive to several other drugs which suppress alcohol intake. Therefore, the similar suppression of alcohol intake induced by NPI-031G in the P and HAD rats is confirming evidence of its alcohol intake suppression activity.

Figure 7:
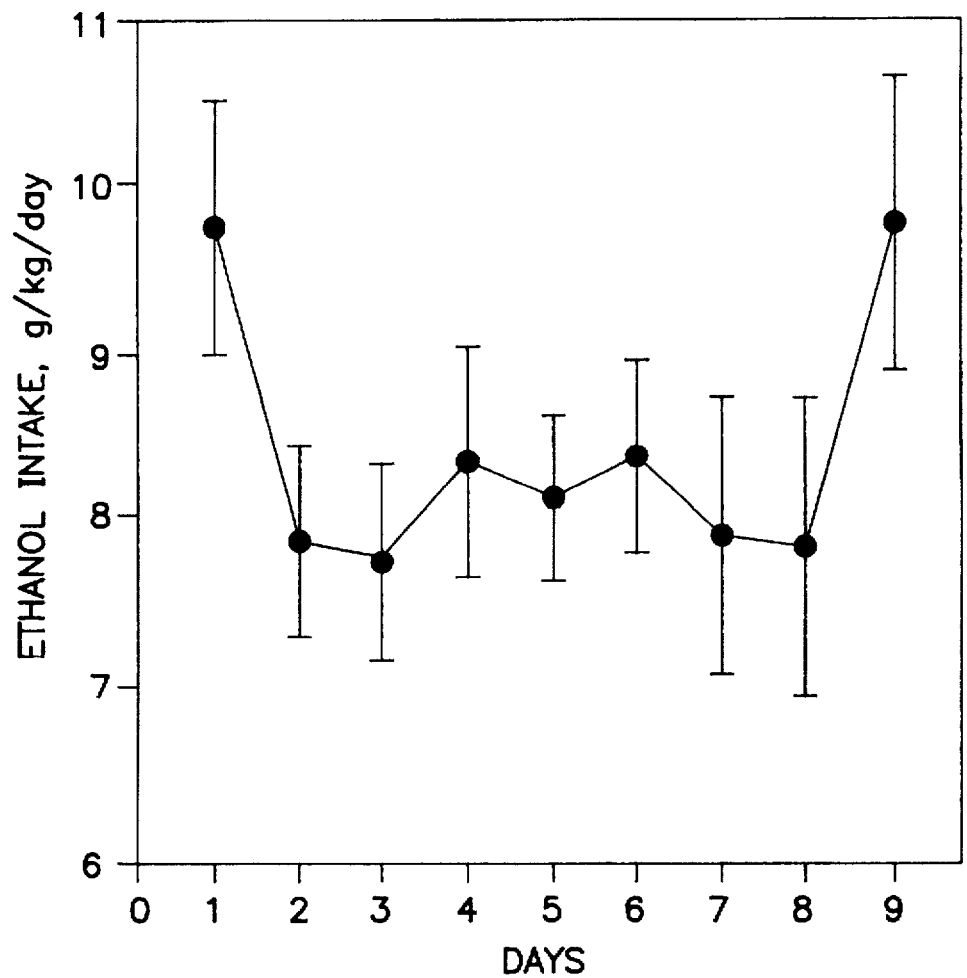
FIG. 7 is a graph which shows the consistent suppression of alcohol intake in HAD Rats by administration of puerarin over a period of a week.

The HAD rats were also given NPI-031G subchronically for seven days to determine whether there might be tolerance and/or sensitization to its suppressant effects on alcohol intake. As can be seen in FIG. 7, which shows the effects of chronic NPI-0361G (Puerarin) treatment on alcohol intake in HAD Rats (NPI-031G was given once daily (150 mg/kg) once daily at 10:00 a.m. for seven consecutive days; Day 1 showing the result for the vehicle (20% DMSO in distilled water); Day 9 showing the intake 48 hours after the last injection), NPI-031G had consistent suppressant effects throughout the 7-day treatment period.

EXAMPLE 19

NPI-031D and NPI-031E in FH Rats

After baseline alcohol intake was established, 8 male FH rats received a single i.p. injection of either control saline or one of the two doses of daidzin and daidzein in a cross-over design. At least 3 days was allowed between injections. All injections were done at 9:30 a.m., and alcohol, water, food, total fluid intakes and alcohol preference were recorded 24 hr after each injection (Table 6).

TABLE 6

Effects of Daidzin and Daidzein I.P. in FH Rats (Mean ± S.E.M.)

| Treatment (mg/kg) | Food (g/kg/day) | Water (g/kg/day) | Alcohol (g/kg/day) | Total Fluid (ml/kg/day) | Preference (% Alcohol Intake) |
|---|---|---|---|---|---|
| Control | 58 ± 3[a] | 54 ± 8[a] | 5.2 ± 0.6[a] | 117 ± 6[a] | 56 ± 5[a] |
| Daidzin | | | | | |
| 50 | 49 ± 4[a] | 75 ± 8[a] | 2.9 ± 0.5[b] | 112 ± 8[a] | 33 ± 5[b] |
| 150) | 53 ± 4[a] | 82 ± 11[a] | 2.5 ± 0.6[b] | 117 ± 6[a] | 29 ± 6[b] |
| Daidzein | | | | | |
| 50) | 46 ± 4[b] | 33 ± 9[a] | 4.9 ± 0.1[a] | 99 ± 8[a] | 58 ± 10[a] |
| 150 | 38 ± 4[b] | 33 ± 12[a] | 5.1 ± 0.8[a] | 98 ± 8[a] | 69 ± 11[a] |

Groups with different superscripts are significantly different from each other.

Results: As shown in Table 6, daidzin, which contains a sugar moiety, significantly reduced alcohol intake and alcohol preference, while daidzein significantly reduced food intake and tended to reduce water intake, without affecting alcohol intake.

EXAMPLE 20

Suppressant Effects of NPI-031L (Genistein) and NPI-031M (Methyl Genistein) in P Rats Six adult male P rats were screened for alcohol intake. After establishment of stable alcohol intake in a continuous access two-bottle choice paradigm for at least 2 months, they received a single i.p. injection of saline (0.0) or one of the three doses (10, 20 and 30 mg/kg) of genistein or methyl genistein at 9:30 a.m. in a random order design. At least 3 days were allowed between injections. Alcohol, water and food intake were measured 24 hr after each injection. As shown by the data in Table 7, the methyl ester of genistein was somewhat more effective than genistein, and both compounds were active at lower doses than found for the isoflavones, daidzin, daidzein, and puerarin. Food, water, and total fluid intake were not significantly affected.

TABLE 7

Effects of Genistein and Methyl Genistein on Alcohol Intake (Mean ± S.E.M., n = 6)
Dose (mg/kg, i.p.)

| Treatment | 0.0 | 10 | 20 | 30 |
|---|---|---|---|---|
| Genistein | 6.9 ± 0.4 | 5.6 ± 0.8 | 5.4 ± 0.4 | 3.9 ± 0.1* |
| Methyl Genistein | 6.9 ± 0.4 | 5.8 ± 0.7 | 4.6 ± 0.6* | 4.2 ± 0.7* |

*Significantly different from control (0.0), p < 0.02.

References

Berg, B. J., Volpicelli, J. R., Alterman, A. I., and O'Brien, C. P. (1990). The relationship between endogenous opioids and alcohol drinking: the opioid compensation hypothesis. Presented at the International Society of Biomedical Research on Alcoholism; 1990 Satellite Symposium on Novel Pharmacological Interventions for Alcoholism; Jun. 16, 1990; Toronto, Ontario.

Keung W-M, Vallee B L: Daidzin and daidzein suppress free-choice ethanol intake by Syrian golden hamsters. Proc Natl Acad Sci USA 90:10008–10012, 1993a.

Keung W M, Vallee B L. Daidzin: A potent selective inhibitor of human mitochondrial aldehyde dehydrogenase. Proc Nat Acad Sci. USA 90:1247–1251, 1993b.

Keung, W. M., Lazo, O., Kunze, L., and Vallee, B. L. Daidzin suppresses ethanol consumption by Syriau golden hamster without blocking acetaldehyde metabolism. Proc. Nat. Acad. Sci. USA 92:8990–8993, 1995.

Lawrin, M. O., Naranjo, C. A., and Sellers, E. M. Identification and testing of new drugs for modulating alcohol consumption. Psychopharmacol. Bull 22:1020–1025, 1986

Li S C: Ben Cho Gang Mu (1590–1596 A.D.)

Litten R. Z. and Allen J. P. Pharmacotherapies for alcoholism: Promising agents and clinical issues. Alcohol. Clin. Exp. Res. 15:620–633, 1991.

McBride, W. J., Murphy, J. M., Lumeng, L., Li, T-K. Serotonin and ethanol preference. In Recent Developments in Alcoholism (Galanter, M., Ed.) vol. 7, pp. 187–209, Plenum Press, New York, 1989.

Meyer, R. E. Prospects for a rational pharmacotherapy of alcoholism. J. Clin. Psychiatr. 50:403–412, 1989.

Naranjo, C. A., Kadlec, K. D., Sanhueza, P., Woodley-Remus, and Sellers, E. M. Fluoxetine differentially alters alcohol intake and other consummatory behaviors in problem drinkers. Clin. Pharmacol. Ther. 47:490–498, 1990.

O'Malley, S. S., Jaffe, A., Chang, G., Wite, G., Schottenfeld, R. S., and Rounsaville, B. J. Naltrexone in the treatment of alcohol dependence: preliminary findings. In: Novel Pharmacological Interventions for Alcoholism (Naranjo, C., ed.), 148–157. Springer, Verlag, New York, 1992a.

O'Malley, S. S., Jaffe, A. J., Chang, G., Schottenfeld, R. S., Meyer R. E., and Rounsaville, B. Naltrexone and coping skills therapy for alcohol dependence: a controlled study. Arch. Gen. Psychiatr. 49:881–887, 1992b.

Overstreet, D. H., Lee, Y. W., Rezvani, A. H., Criswell, H. E. Reduction in alcohol intake in alcohol-preferring rats by the Chinese herbal medicine XJL. Alcohol. Clin. Exper. Res. 17:483, 1993

Overstreet, D. H., Lee, Y. W., Rezvani, A. H., Criswell, H. E. Suppression of alcohol intake following administration of the Chinese herbal medicine, NPI-028, and its derivatives. Alcohol. Clin. Exper. Res (In press), 1996.

Rezvani A H, Garges P, Overstreet D H: Enhanced alcohol intake in Fawn-Hooded rats after withdrawal from alcohol. Society for Neuroscience Abstracts 18:540, 1992.

Rezvani A H, Lee Y-W, Overstreet D H: Effects of Chinese herbal extracts on alcohol intake in alcohol-preferring rats. Alcohol Clin Exper Res 18:488, 1994.

Rezvani A H, Overstreet D H, Janowsky D S: Drug-induced reductions in ethanol intake in alcohol preferring and Fawn-Hooded rats. Alcohol Alcohol Suppl. 1:433–437, 1991.

Rezvani A H, Overstreet D H, Janowsky D S: Genetic serotonin deficiency and alcohol preference in the Fawn-Hooded rats. Alcohol Alcohol 25:573–575, 1990.

Rezvani A H, Overstreet D H, Lee Y W: Attenuation of alcohol drinking by Ibogaine in three strains of alcohol-preferring rats. Pharmacol Biochem Behav. 52:615–620, 1995a.

Rezvani A H, Overstreet D H, Pucilowski O, Hu Y H, Lee Y W: Chinese herbal medicine NPI-028 reduces alcohol intake without inducing taste aversion. Alcohol Clin Exp Res 19:15A, 1995b.

Sellers, E. M.; Higgins, G. A.; and Sobell, M. B. 5-HT and alcohol abuse. Trends Pharmacol. Sci. 1368–75, 1992.

Sinclair J D, Li, T-K. Long and short alcohol deprivation: effects on AA and P alcohol preferring rats. Alcohol 6:505–509, 1989.

Soyka, M. (1995) Anti-craving drugs in relapse prevention of alcoholism Nervenheillkunde 14: 84–86, 1995.

Volpicelli, J. R., Alterman, A. I., Hayashida, M., and O'Brien, C. P. Naltrexone in the treatment of . . .

Soyka, M. (1995a) Anti-craving drugs in relapse prevention of alcoholism (in German). Sucht (in press).

Volpicelli, J. R., Alterman, A. I., Hayashida, M., and O'Brien, C. P. Naltrexone in the treatment of alcohol dependence. Arch. Gen. Psychiatr., 49:876–880, 1992.

Volpicelli, J. R., O'Brien, C. P., Alterman, A. I., and Hayashida, M. Naltrexone and the treatment of alcohol-dependence:initial observations. In:opiods, Bulimia and Alcohol Abuse and Alcoholism (Reid, L. D., ed.), pp. 195–214. Springer-Verlag, New York, 1990.

Xie C-I, Lin R C, Antony V, Lumeng L, Li T-K, Mai K, Liu C, Wang Q-d, Zhao Z-h, Wang G-f: Daidzin, an antioxidant isoflavonoid, decreases blood alcohol levels and shortens sleep time induced by ethanol intoxication. Alcohol Clin Exp Res 18:1443–1448, 1994.

The preceding examples can be repeated with similar success by substituting the generically or specifically described reactants and/or operating conditions of this invention for those used in the preceding examples.

Applicants wish to incorporate by reference the inventors' paper entitled "Suppression of Alcohol Intake After Administration of Chinese Herbal Medicine, NPI-028 and Its Derivatives", *Alcoholism, Clinical, and Experimental Research*, Vol. 20, No. 2, pp. 221–227, 1996.

From the foregoing descriptions, one skilled in the art can easily ascertain the essential characteristics of this invention and, without departing from the spirit and scope thereof, can make various changes and modifications of the invention to adapt it to various usages and conditions.

What is claimed is:

1. A method of treating alcohol dependence which comprises administering to a patient, a pharmaceutical composition comprising, in admixture with a pharmaceutically acceptable carrier, an amount effective to treat alcohol dependence of at least one isoflavenoid-C-glycoside of the formula (I) isolated to a purity of 90% or more:

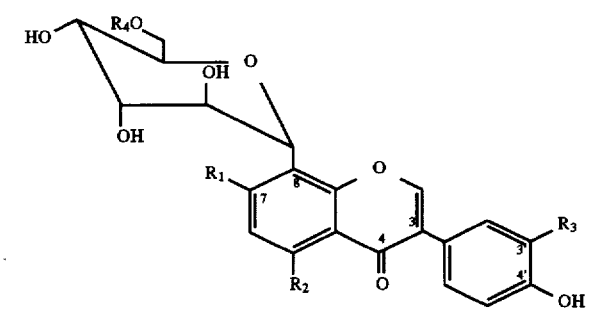

wherein $R_1$=H or OH; $R_2$=H or OH; $R_3$=H, OH or OR' wherein R' is lower alkyl; and $R_4$=H, glucosyl or 1,6-apiosyl.

2. A method according to claim 1, wherein $R_1$=OH; $R_2$ and $R_4$=H; and $R_3$=H, OH or $OCH_3$.

3. A method according to claim 1, wherein the composition comprises puerarin.

4. A method according to claim 1, wherein puerarin is the only isoflavonoid-C-glycoside in the composition.

5. A method according to claim 1, wherein the composition is administered orally.

6. A method according to claim 1, wherein the composition is administered at least once daily.

7. A method according to claim 1, wherein puerarin is the only isoflavonoid-C-glycoside in the composition and the composition is administered orally at least once daily.

8. A method according to claim 6, wherein the composition is administered orally.

9. A method according to claim 1, wherein the composition is administered at least once daily until consumption of alcohol by the patient has ceased.

10. The method of claim 1, wherein the pharmaceutical composition is administered in successive spaced doses.

11. The method of claim 1, wherein the pharmaceutical composition is administered in a dose containing 1 to 500 mg of the at least one isolated isoflavenoid-C-glycoside of formula (I).

* * * * *